United States Patent
Giardino et al.

(10) Patent No.: US 7,566,295 B2
(45) Date of Patent: Jul. 28, 2009

(54) ELECTROMAGNETIC FIELD STIMULATOR DEVICE FOR ANATOMIC BIOPHYSICAL CHONDROPROTECTION

(75) Inventors: Roberto Giardino, Bologna (IT); Ruggero Cadossi, Carpi (IT); Stefania Setti, Carpi (IT)

(73) Assignee: IGEA S.R.L. (IT)

( * ) Notice: Subject to any disclaimer, the term of this patent is extended or adjusted under 35 U.S.C. 154(b) by 44 days.

(21) Appl. No.: 10/578,658

(22) PCT Filed: Nov. 10, 2004

(86) PCT No.: PCT/EP2004/052914

§ 371 (c)(1), (2), (4) Date: Dec. 1, 2006

(87) PCT Pub. No.: WO2005/044375

PCT Pub. Date: May 19, 2005

(65) Prior Publication Data

US 2007/0173681 A1   Jul. 26, 2007

(30) Foreign Application Priority Data

Nov. 11, 2003   (IT) ................ TO2003A0893

(51) Int. Cl.
*A61N 1/00* (2006.01)

(52) U.S. Cl. .......................................... 600/14

(58) Field of Classification Search ............... 600/9–15; 128/898–899
See application file for complete search history.

(56) References Cited

U.S. PATENT DOCUMENTS

| | | | |
|---|---|---|---|
| 3,820,534 A | 6/1974 | Kraus et al. | 128/82.1 |
| 4,587,957 A | 5/1986 | Castel | 128/1.3 |
| 5,211,622 A * | 5/1993 | Liboff et al. | 600/9 |
| 6,290,638 B1 * | 9/2001 | Canedo et al. | 600/9 |
| 2003/0093028 A1 | 5/2003 | Spiegel | 604/20 |

FOREIGN PATENT DOCUMENTS

EP   1 138 348 A2   10/2001

OTHER PUBLICATIONS

International search Report PCT/EP2004/052914 dated Feb. 11, 2005.

* cited by examiner

*Primary Examiner*—Samuel G Gilbert
(74) *Attorney, Agent, or Firm*—Ostrolenk Faber LLP

(57) ABSTRACT

Electromagnetic field stimulator device in which a current generator device supplies a solenoid with current the waveform of which includes the repetition of a ramp having a certain slope. This current causes the generation of an electromagnetic field that induces on a control probe irradiated by the electromagnetic field, an induced voltage of markedly constant amplitude during the ramp-like linear growth period of the current. This electromagnetic field is used to preserve the integrity of articular cartilage subject to degeneration.

15 Claims, 4 Drawing Sheets

ELECTROMAGNETIC FIELD STIMULATOR DEVICE FOR ANATOMIC BIOPHYSICAL CHONDROPROTECTION

CROSS REFERENCE TO RELATED APPLICATION

The present application is a 35 U.S.C. §§ 371 national phase conversion of PCT/EP2004/052914, filed 10 Nov. 2004, which claims priority of Italian Patent Application No. TO2003A 000893, filed 11 Nov. 2003. The PCT International Application was published in the English language.

TECHNICAL FIELD

This invention concerns an electromagnetic field stimulator device for Anatomic Biophysical Chondroprotection.

BACKGROUND ART

Electromagnetic field stimulator devices, in which a generator of pulsating, variable current is able to feed at least one solenoid for generating an electromagnetic field directed onto a portion of the human body comprising bone tissue, are well known.

For example, American patent U.S. Pat. No. 3,820,534 published in 1974 describes a device able to allow the growth and repair of bone tissue via the electromagnetic field generated by a solenoid powered by an alternating electric signal with a frequency of less than 50 Hz.

Currently known devices are not capable of protecting articular cartilage from degeneration, or rather are not capable of efficaciously operating on the integrity of cartilaginous tissue, activating a preserving effect against the degradation of the cartilage itself.

As is known, the degeneration of articular cartilage manifests itself very frequently and it progressively worsens with age. Suffice it to think that alterations of the cartilage surface only manifest themselves in 5% of the population below 25 years of age, while they are present in more than 80% of people over 75. However, cartilage degeneration is not just a consequence of ageing, but also the end result of a complex series factors related to problems of a biological nature and/or mechanical problems.

Articular cartilage does not possess significant self-healing capabilities other than for small lesions when in youth. The quality and mechanical properties of articular cartilage can only diminish in the course of life.

Of the causes that can damage articular cartilage, we can identify those with a mechanical basis and those with a biological basis Mechanical causes can be acute or chronic, depending respectively on whether the result of a severe trauma or an alteration of the load axis.

The biological causes are mainly due to the presence of inflammation ascribable to subchondral bone and intraarticular structures (synovial in particular). Inflammatory processes produce a strong catabolic effect on cartilage, because the inflammatory cells synthesize and release pro-inflammatory cytokines (interleukin 1 and 6, and TNF-α) that inhibit the synthesis of proteoglycans by the chondrocytes and increase the synthesis of enzymes (matrix metalloproteinase 3, MMP3), which in turn degrade the cartilaginous matrix. The inflammatory response of the articular structures is often the consequence of acute or chronic traumas, distortions, avascular bone necrosis of the subchondral bone, bone marrow edema of the condyles, and side effects of open or arthroscopic surgery.

On the basis of these premises, it becomes fundamental to have a therapy at hand capable of locally controlling the inflammation, at both the subchondral bone and articular structure levels. The therapy must also be able to act directly on the chondrocites in the depth of the cartilage to prevent the catabolic effects of the inflammatory cytokines on the chondrocite and on the matrix, to facilitate anabolic activities and the synthesis of proteoglycans. The simultaneous treatment of cartilage, subchondral bone tissue and articular fleshy structures is only practicable with physical means.

Based on this premise, the need is thus felt for realizing a device that is capable of putting that specified above into effect.

DISCLOSURE OF INVENTION

The foregoing object is achieved by this invention, which concerns an electromagnetic field device for Anatomic Biophysical Chondroprotection Therapy, in which the means of current generation are suitable for powering at least one solenoid to generate an electromagnetic field directed onto a part of the human body including cartilaginous tissue, characterized by the fact that said means of current generation supplies said solenoid with current having a waveform that includes the repetition of a ramp with a certain slope; said current causing the generation of an electromagnetic field that induces on a control probe irradiated by this electromagnetic field, an induced voltage Vin of markedly constant amplitude during the ramp-like linear growth period of the current in the solenoid.

BRIEF DESCRIPTION OF THE DRAWINGS

The invention will now be illustrated with particular reference to the enclosed figures that represent a preferred, non-limitative form of embodiment in which.

BEST MODE FOR CARRYING OUT THE INVENTION

Figures 1, 2:
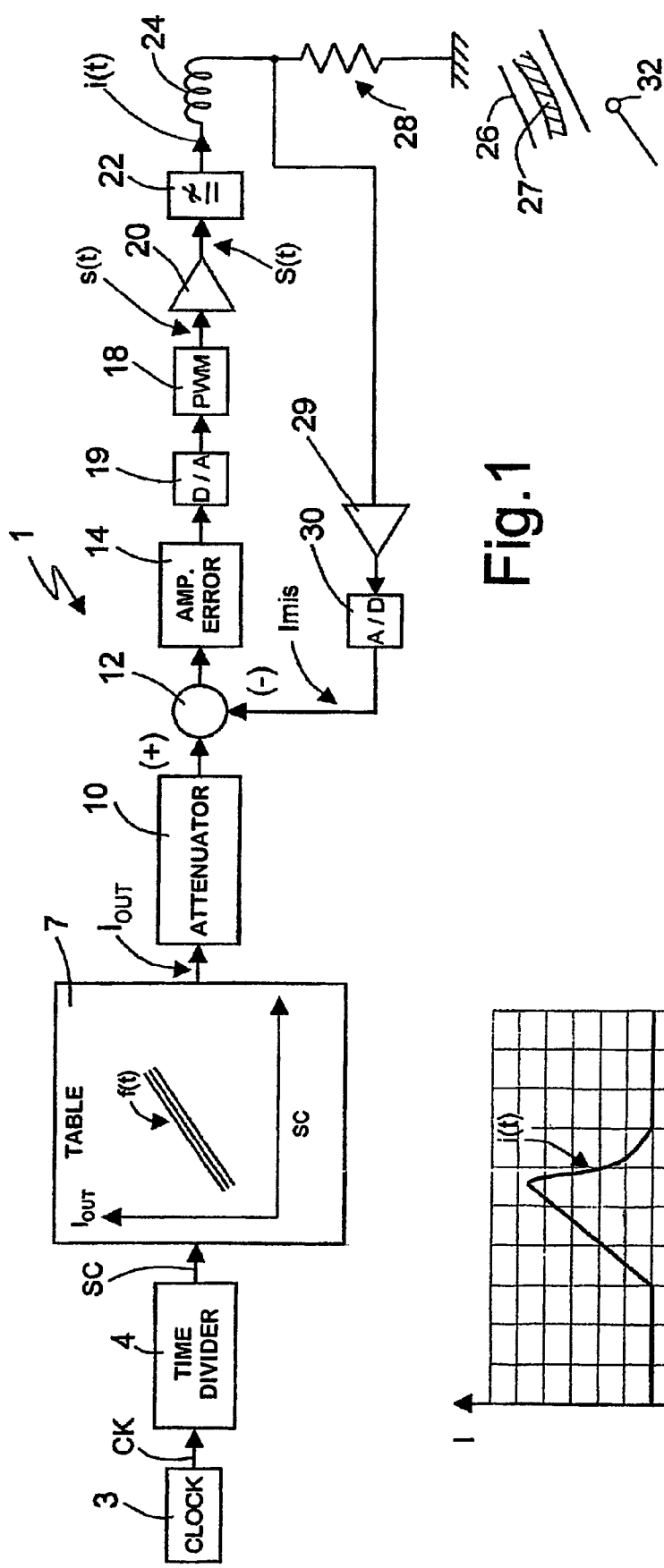
FIG. 1 illustrates a simplified wiring diagram of an electromagnetic field stimulator device for Anatomic Biophysical Chondroprotection realized according to the principles of this invention.
FIG. 2 illustrates the time modulation of two quantities controlled by the stimulator device in accordance with this invention.

In FIG. 1, an electromagnetic field stimulator device for Anatomic Biophysical Chondroprotection (CBA) is generally indicated by 1.

In particular, the stimulator device 1 includes a synchronizing signal generator 3 suitable for producing an output signal ck with a constant frequency, for example 16 MHz, used as an internal reference. The device 1 also includes a time-division circuit 4 receiving the synchronization signal ck in input, and able to time divide the signal ck to generate a scanning signal sc fed in input to a table 7.

The table 7 contains a number of selectable maps, each of which implements a function f(t) that provides, for each value of the scanning signal sc in input, an output value Iout that expresses a target current intensity.

In greater detail, the function f(t) is linear and represents a ramp with a certain slope that provides, for increasing values of the scanning signal sc in input, linearly increasing intensity values for the target current Iout. At the end of scanning the function, the function is scanned again starting from the beginning of the ramp. In this way, following operation of the synchronizing signal generator 3 and the time divisor 4, the output signal Iout presents a saw-tooth profile comprising the repetition of a ramp that expresses increasing values of current intensity.

The device 1 also includes an attenuator circuit 10 at receives the signal Iout in input and feeds it to a subtraction block 12, which performs the arithmetic difference between the same signal Iout and a signal Imis that expresses the real current intensity. The output of the subtraction block 12 (ring error) is fed to the input of an error amplifier 14 (for example, a Proportional-Integral-Derivative circuit) which has an output that pilots a pulse width modulator block (PWM) 18 via a digital/analogue converter 19.

The PWM block 18 generates an alternating analogue signal s(t) in output with a constant frequency (for example, 250 KHZ and adjustable duty cycle. For example, the signal s(t) could have a square waveform.

The duty cycle of the signal s(t) is modified as a function of the numeric value fed in input to the PWM block 18; in particular, the duty cycle of the signal s(t) increases with the increase in the numerical value of the signal fed in input to the PWM block 18.

The analogue signal s(t) is fed in input to an output amplifier stage 20 (of known type), which generates an output power signal S(t) that feeds a solenoid 24 via a low-pass filter 22. The low-pass filter 22 is suitable for eliminating spurious components from the power signal S(t); this filter 22 is advantageous as the power signal S(t) generates high-order harmonic components.

The solenoid 24 generates a special type of electromagnetic field (detailed further on) that is directed onto a portion of a human body 26 comprising a portion of cartilage 27, especially articular cartilage.

The solenoid 24 is realized in a manner such that the physical stimulus can follow the shape of the anatomic surfaces of the portion of the human body 26 and can penetrate in depth into the cartilage and subchondral bone.

In particular, the solenoid 24 can be opportunely made using multiple sheets of a flexible material (for example, three sheets of Kapton, 50 micron thick), on the faces of which copper tracks have been deposited, via a photoengraving process, which form the turns of the solenoid 24 itself. For example, the copper tracks can be conveniently distanced 0.3 mm from each other, be 1.7 mm wide and 35 μm thick.

The distance between the copper tracks and their thickness and width render the solenoid 24 particularly flexible, thereby permitting the physical stimulus to be transmitted over the entire zone to be treated in a uniform manner all around the zone of application, following the shape of the anatomic surfaces.

In particular, the electromagnetic field induced by the solenoid 24 distributes itself over the portion of the human body 26 in such a way to include not just the cartilaginous tissue in all of its extension and all of its thickness, but also the various articular surfaces, meniscuses, ligaments, symposia, subchondral bone, etc.

A detector device 28 (for example, a shunt resistor or a Hall-effect sensor) detects the value of the current i(t) running in the solenoid 24. The output of the detector device 28 feeds a feedback amplifier 29, the output of which, in turn, feeds an analogue/digital converter 30, which produces the signal Imis that expresses the measured value of the current running in the solenoid 24.

The attenuator circuit 10 proportionally reduces all of the points in table 7 by a programmable parameter IPK to achieve a uniformly scaled current profile. In particular, if the value of the parameter IPK is equal to zero, no limitation on the current feeding the solenoid 24 is applied, which is thus free of restrictions, i.e. it is the maximum load request. However, if the parameter IPK is non-zero, this parameter IPK represents instead the maximum peak value for the current generated by the solenoid 24. Each value in the table 7 will therefore contribute to realizing a current value proportional to the maximum peak value expressed by the parameter IPK.

In use, after the device 1 is switched on, a signal Iout is generated that has a reference function and comprises the repetition of a ramp that represents increasing values of current intensity. The reference value Iout can also be altered by selecting a different map in table 7.

The PWM block 18 receives a variable signal in input and consequently changes the duty cycle of the power signal S(t) in function of this input signal, in order to induce a current in the solenoid 24 follows the modulation established by the signal Iout, which thus performs a reference function.

The intensity of the current in the solenoid 24 is therefore regulated via the variation of the duty cycle of the power signal S(t).

In this way, a current generator is realized that feeds the solenoid 24 with a current i(t) whose waveform includes the repetition of a ramp (FIG. 2) having a predetermined and constant slope.

This current causes the generation of an electromagnetic field that induces on a control probe 32 (FIG. 1) irradiated by this electromagnetic field, an induced voltage Vin of markedly constant amplitude during the ramp-like linear growth period of the current in the solenoid 24.

The induced voltage is in fact proportional over time to the derivative of the signal feeding the solenoid 24.

For example, an induced voltage Vin having constant amplitude between 1 and 4 Millivolt during the entire active period of piloting the solenoid 24 can be usefully realized.

The feedback system of the device 1, constituted by the detector device 28, the feedback amplifier 29 and the analogue/digital converter 30, accomplishes continuous monitoring of the current i(t) circulating in the solenoid 24 and compares (subtraction block 12) the measured current value Imis with that "mapped" in the table 7, i.e. with the signal Iout.

In the case of variances from these values, due to small variations in impedance (resistance and/or inductance) of the solenoid 24 for example, the feedback system immediately takes care of, via the ring error signal, the correction to the duty cycle of the power signal S(t) and thus the value of the current feeding the solenoid 24, in order to maintain the waveform of the induced voltage Vin unaltered.

Experimental results of the applicant have shown that the device 1 achieves Anatomic Biophysical Chondroprotection, or rather that it is capable of: preserving the integrity of cartilage, controlling inflammatory articular processes dependent on both subchondral bone and articular structures, protecting the chondrocite and the cartilaginous matrix from the catabolic effects of inflammatory cytokines, favouring cartilage trophism stimulating the chondrocitic metabolism and the synthesis of proteoglycans, and acting directly on subchondral bone protecting trophism and guaranteeing integration in the presence an autologous transplant. In particular, Anatomic Biophysical Chondroprotection finds favourable application in human beings for the treatment of inflammatory and degenerative conditions regarding articular cartilage and subchondral bone of the main articulations, especially the knee, in all conditions of bone marrow edema regarding the subchondral bone of femoral condyles, in the healing and integration of bone grafts after ligament reconstruction operations on the fibrous flexor sheaths of the knee, and in the healing and integration of knee joint osteo-cartilaginous grafts.

These effects are confirmed by a series of studies carried out both in vitro and in vivo, the results of which are detailed below.

In vitro Effects: Inflammation Control

Anatomic Biophysical Chondroprotection acts in a specific manner on the adenosinic receptors $A_{2A}$ of the cellular membrane of pro-inflammatory cells, neutrophils, rendering then available to binding with adenosine. Within the sphere of adenosinic receptors, the receptors $A_{2A}$ are those of greater anti-inflammatory effect.

The bonding with adenosine causes: inhibition of the production of pro-inflammatory cytokines, reduction in the synthesis of free radicals, increase in the production of ATP and cytokines with anti-inflammatory action, TGFβ, and the inhibition of cicloxygenase 2 activity.

The kinetic studies carried out by the applicant have shown how the stimulator device implemented in accordance with this invention permits an anti-inflammatory effect to be achieved. In cases of inflammation, by using the device 1 it is in fact possible to activate the adenosinic receptors on the cell membrane via the generated biophysical stimulus.

Figure 3:
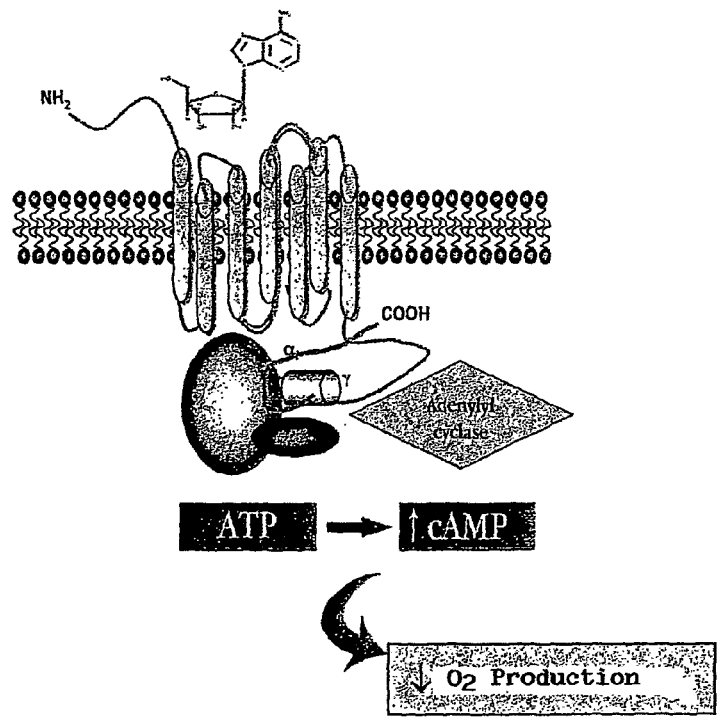
FIG. 3 illustrates intracellular events activated by the stimulator device in accordance with this invention.

FIG. 3 shows in detail the transduction mechanism of the biophysical signal on the adenosinic receptors $A_{2A}$ of the cell membrane and the intracellular events activated by the bonding of adenosine with the associated receptor and generating the anti-inflammatory action.

Figure 4:
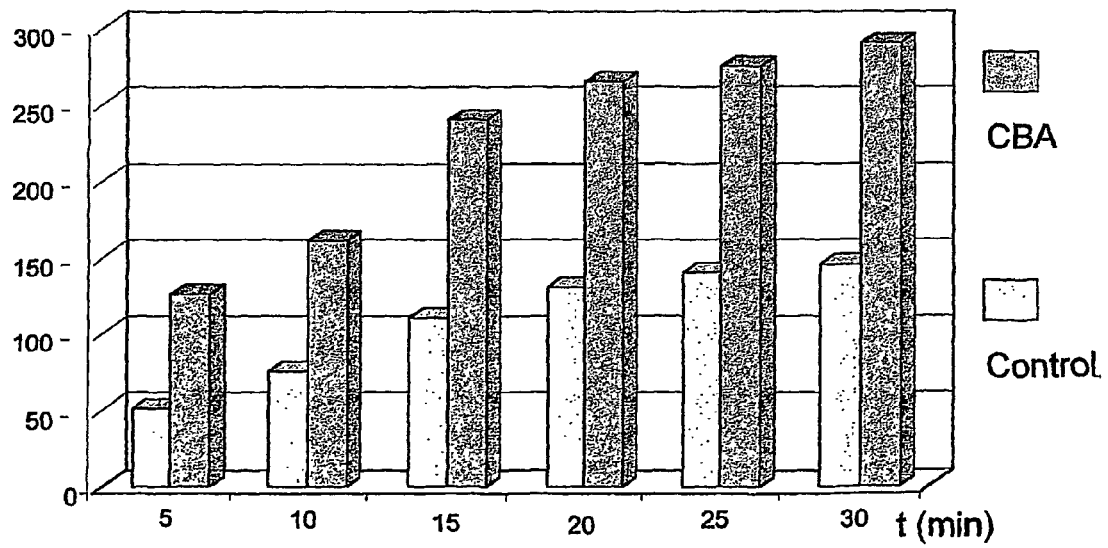
FIGS. 4 and 5 show histograms regarding the differences that are found at intracellular level between regions treated with the stimulator device in accordance with this invention and regions not subjected to treatment, FIGS. 6*a* and 6*b* respectively show an image of an untreated articular region and an image of an articular region treated with the stimulator device in accordance with the invention.

FIG. 4 shows instead a histogram representing the number of bonds formed between adenosine and the adenosinic receptor $A_{2A}$ on the membrane of human neutrophils in the presence of and in the absence of treatment with the device 1, as a function of time. As can be seen, the number of bonds formed and the consequent anti-inflammatory action is roughly doubled in the presence of the stimulation treatment provided via the device 1 realized according to the principles of this invention.

In vitro Effects: Anabolic Effect on Cartilage

Anatomic Biophysical Chondroprotection exerts an anabolic action on cartilage in the presence of inflammatory cytokines (IL-1).

Explants of articular cartilage cultivated in the presence of inflammatory cytokines (IL-1) face an increase in catabolic activities, which accompanies degradation of the cartilaginous matrix and the decrease in synthesis of proteoglycans. If however, the explants are exposed to the electromagnetic field generated by the device 1 the catabolic effect of the inflammatory cytokines on the matrix is completely inhibited and the integrity of the cartilaginous matrix, as well as the proteoglycans synthesis capacity, is preserved.

Figure 5:
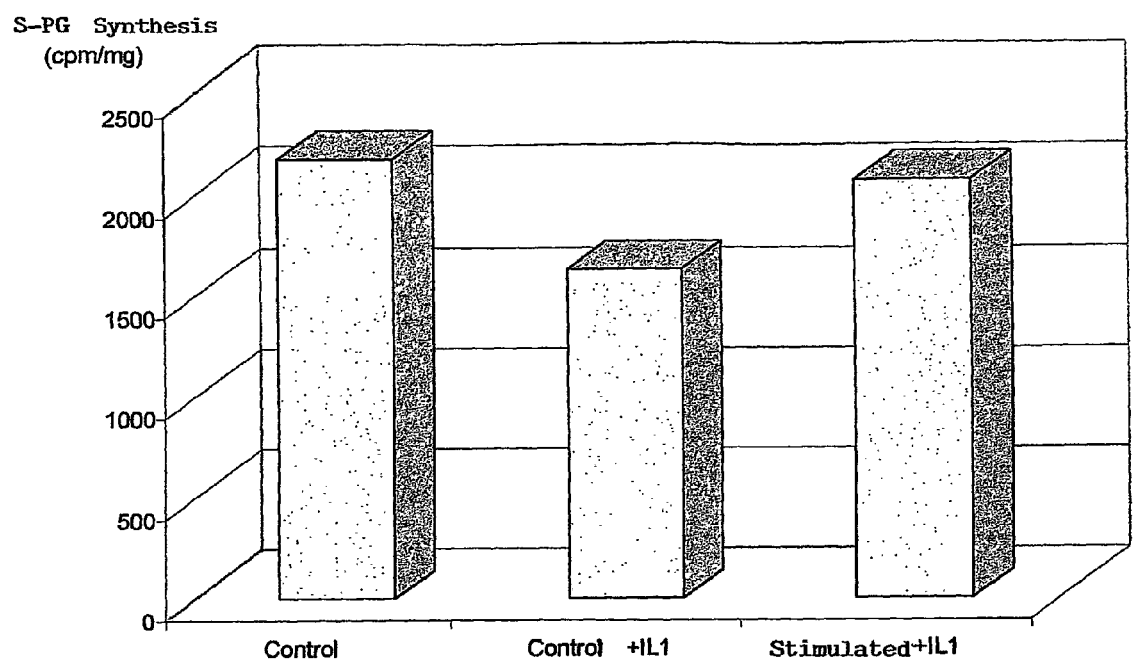

FIG. 5 illustrates a histogram that shows the synthesis capacity of proteoglycans (S-PG) in explants of articular cartilage in the following conditions: control conditions, condition of exposure to the catabolic effect of the inflammatory cytokines and the condition of exposure to the catabolic effect of the inflammatory cytokines combined with stimulation via the device 1 in accordance with the invention. As can be noted, the synthesis capacity of proteoglycans is found to be heavily compromised due to the inflammatory cytokines, but returns to more-or-less normal values, equal to the control ones, in the presence of the Anatomic Biophysical Chondroprotection effect generated by the stimulation device 1.

In vivo Effects: Inhibition of Articular Cartilage Degeneration

Anatomic Biophysical Chondroprotection inhibits the degenerative processes affecting articular cartilage that are observed with ageing. Utilizing the model of spontaneous osteoarthrosis in the guinea pig and quantifying the damage to the articular cartilage according to the Mankin classification, a strong chondroprotective effect linked with the stimulation supplied by the device 1 in accordance with the invention, was revealed.

Figure 6A:
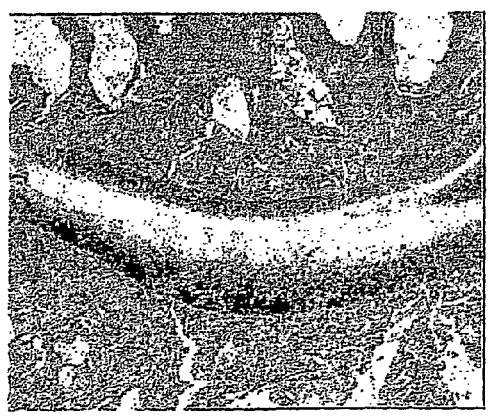
Figure 6B:

FIG. 6a shows evident signs of cartilage degeneration that are found in control animals due to ageing. FIG. 6b instead shows cartilage treated with the Anatomic Biophysical Chondroprotection therapy in which the absence of degeneration is evident. In particular, the thickness of the cartilage is maintained at normal levels, the colouring of the cartilaginous matrix appears intense and phenomena of fibrillation are not observed.

In vivo Effects: Healing of Subchondral Bone Tissue

Anatomic Biophysical Chondroprotection exerts a healing action on subchondral bone tissue.

The healing of serious cartilage lesions can be carried out with various surgical options, the success on which depends in large measure to the characteristics of the subchondral bone tissue.

The action of the device 1 in accordance with this invention brings about rapid healing of subchondral bone tissue and prevents phenomena of bone reabsorption, creating optimal conditions for the viability of the overlaying articular cartilage. In addition, in the presence of a bone transplant, it favours the early anchorage of the graft itself, guarantees good integration of the transplanted bone tissue, prevents the formation of small bone cysts, and hence guarantees stability of the bone graft. It should be noted that in this regard, in the case of osteo-cartilaginous transplants, the early anchorage of subchondral bone is the necessary prerequisite for the viability and the preservation of the transplanted cartilage.

Figure 7A:
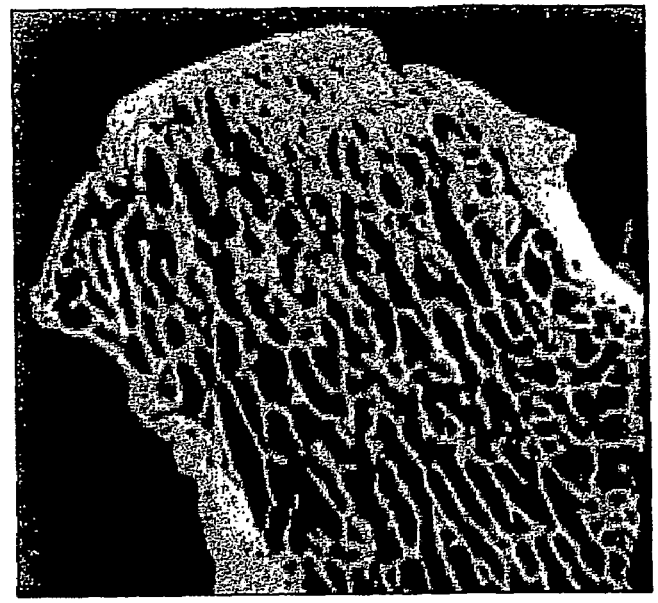
FIGS. 7*a* and 7*b* show images of an osteo-cartilaginous graft treated with the stimulator device in accordance with the invention.
Figure 7B:

Two images are shown in FIGS. 7a and 7b regarding an osteo-cartilaginous graft on an animal model treated with the Anatomic Biophysical Chondroprotection therapy six months after the grafting operation. In particular, in the microradiographic image in FIG. 7a the complete integration of the subchondral bone may be noted, while in the histological image in FIG. 7b the viability of the transplanted cartilage can be observed, which exhibits an adequate thickness and intense colouring of the cartilaginous matrix.

From examination of the characteristics of the electromagnetic field stimulator device for Anatomic Biophysical Chondroprotection realized in accordance with this invention, the benefits that can be achieved with it are evident.

In particular, by using the above-described stimulator device, it is possible to program the pilot current profile of the solenoid that generates the electromagnetic stimulation field point by point and it is also possible to create different current profiles by simply selecting different pilot maps, so as to take into account the various types of treatment and/or different solenoids used. In particular, the possibility of being able to realize an "ad hoc" current profile for each different solenoid used is advantageous.

Furthermore, this precise control of the pilot current permits an induced voltage to be generated that is as constant as possible and of adequate amplitude for the type of treatment.

Finally, via the implemented feedback system it is possible to react automatically to load changes, due to changes in impedance related to changes in temperature or to the tolerance of components for example, so as to ensure the stimulator device high operational stability and thus safeguard the therapeutic effectiveness of the stimulator device itself in all conditions.

The invention claimed is:

1. An electromagnetic field stimulator device for Anatomic Biophysical Chondroprotection, comprising:
   means of current generation for powering at least one solenoid to generate an electromagnetic field directed on a part of the human body including cartilaginous tissue,
   wherein said means of current generation supplies said solenoid with current (i(t)) having a waveform that includes the repetition of a linear ramp with a certain slope; said current (i(t)) causing the generation of an electromagnetic field that induces on a control probe irradiated by said electromagnetic field, a voltage (Vin) of markedly constant amplitude during the ramp-like linear growth period of said current (i(t)).

2. A device according to claim 1, wherein said means of current generation include at least one table in which at least one function (f(t)) is stored that provides, for each value of a scanning signal in input (sc), an output value that expresses a target current intensity (Iout), the said function f(t) being a linear one and representing a ramp with a certain slope that supplies, for increasing values of said scanning signal in input (sc), linearly increasing values of said target current intensity (Iout).

3. A device according to claim 2, wherein said table includes a plurality of functions (f(t)) of different, selectable types.

4. A device according to claim 2, further comprising timer devices suitable for generating said scanning signal in input (sc).

5. A device according to claim 2, further comprising attenuator devices having their input communicating with the output of said table, said attenuator devices being suitable for reducing the value of said target current intensity (Iout) in function of a programmable parameter (IPK) to limit the maximum value of said current (i(t)) feeding said solenoid.

6. A device according to claim 1, further comprising a feedback system for continuous monitoring of said current (i(t)) present in said solenoid, and comparing a measured current value (Imis) with a reference value (Iout);
   wherein in cases of variances between said measured current and reference values, due to changes in impedance of said solenoid, said feedback system automatically adjusts the value of said current (i(t)) feeding said solenoid in order to maintain the waveform of said induced voltage (Vin) unaltered.

7. A device according to claim 6, wherein said feedback system includes:
   detector devices suitable for supplying said measured current value (Imis), and
   subtraction devices suitable for generating an error signal in function of said measured current value (Imis) and of said reference value (Iout).

8. A device according to claim 7, wherein a generator circuit is provided that receives said error signal in input and generates an alternating analogue power signal (S(t)) having a fixed frequency and variable duty cycle in function of said error signal, said variable duty cycle being suitable for regulating the intensity of said current (i(t)).

9. A device according to claim 8, wherein said generator circuit includes a pulse width modulator.

10. A device according to claim 8, further comprising low-pass filter devices between the output of said generator circuit and said solenoid.

11. A device according to claim 1, wherein said solenoid is made from a plurality of sheets of a flexible material to be adapted to the shape of said portion of the human body.

12. A method for Anatomic Biophysical Chondroprotection, comprising the steps of:
    providing the current generating means of claim 1,
    generating an electromagnetic field; and
    applying the electromagnetic field to a portion of the human body including cartilaginous tissue, wherein said step of generating an electromagnetic field includes the step of:
    powering a solenoid with current (i(t)) from said current generating means having a waveform that includes the repetition of a ramp with a certain slope, said current (i(t)) causing the generation of an electromagnetic field that induces on a control probe irradiated by said electromagnetic field, a voltage (Vin) of markedly constant amplitude during the period of ramp-like linear growth of said current (i(t)).

13. A method according to claim 12, wherein said current (i(t)) presents an intensity and said solenoid presents a configuration such that said electromagnetic field penetrates in depth into said portion of the human body until it permeates said portion of cartilage and a portion of subchondral bone associated with said portion of cartilage over their entire thickness and in their entire extension, to activate at intracellular level a process selected from at least one of:
    a process of articular inflammation control regarding both subchondral bone and the articular structures,
    a process of articular inflammation control capable of acting in a specific manner on the adenosinic receptors A2A of the cell membrane of pro-inflammatory cells, neutrophils, doubling the number of bonds with adenosine,
    a process of inhibiting the catabolic effect of inflammatory cytokines acting directly on the chondrocite and on the cartilaginous matrix,
    a process of increasing the metabolic activity of chondrocites and the synthesis of proteoglycans,
    a process of inhibiting degeneration of articular cartilage, preserving the integrity of the same articular cartilage,
    a process of rapid healing of subchondral bone tissue,
    a process of healing bone marrow edema regarding the subchondral bone of femoral condyles, and
    a process of healing and integration of bone grafts after ligament reconstruction operations on the fibrous flexor sheaths of the knee.

14. A method according to claim 12, wherein said current presents an intensity and said solenoid presents a configuration such that said electromagnetic field penetrates in depth into said portion of the human body until it permeates said portion of cartilage and a portion of subchondral bone associated with said portion of cartilage over their entire thickness and in their entire extension, to activate, in the presence of an osteo-cartilaginous graft, a preservation process for the viability of said portion of cartilage and trigger an effect selected from at least one of:

inhibition of reabsorption phenomena on the underlying bone, rapid anchorage of graft, good osteointegration of graft, and inhibition of the formation of bone cysts.

15. A method according to claim 12, wherein said solenoid is made from a plurality of sheets of a flexible material to be adapted to the shape of said portion of the human body.

* * * * *